(12) United States Patent
Hotani

(10) Patent No.: US 10,471,270 B2
(45) Date of Patent: Nov. 12, 2019

(54) MAGNETIC STIMULATION DEVICE

(71) Applicant: Teijin Pharma Limited, Tokyo (JP)

(72) Inventor: Yurika Hotani, Tokyo (JP)

(73) Assignee: Teijin Pharma Limited, Tokyo (JP)

(*) Notice: Subject to any disclaimer, the term of this patent is extended or adjusted under 35 U.S.C. 154(b) by 282 days.

(21) Appl. No.: 15/524,324

(22) PCT Filed: Dec. 24, 2015

(86) PCT No.: PCT/JP2015/085966
§ 371 (c)(1),
(2) Date: May 4, 2017

(87) PCT Pub. No.: WO2016/104578
PCT Pub. Date: Jun. 30, 2016

(65) Prior Publication Data
US 2017/0333725 A1    Nov. 23, 2017

(30) Foreign Application Priority Data
Dec. 25, 2014  (JP) .................................. 2014-262628

(51) Int. Cl.
*A61N 2/02*  (2006.01)
*A61N 2/00*  (2006.01)

(52) U.S. Cl.
CPC ............. *A61N 2/006* (2013.01); *A61N 2/008* (2013.01); *A61N 2/02* (2013.01)

(58) Field of Classification Search
CPC ........... A61N 2/006; A61N 2/008; A61N 2/02
See application file for complete search history.

(56) References Cited

U.S. PATENT DOCUMENTS 4,548,208 A * 10/1985 Niemi ...................... A61N 2/02
                                                           600/14
2006/0094924 A1    5/2006 Riehl
(Continued)

FOREIGN PATENT DOCUMENTS

EP    1 988 479 A2    11/2008
EP    2 444 119 A1    4/2012
(Continued)

OTHER PUBLICATIONS

Communication dated Oct. 27, 2017, from European Patent Office in counterpart application No. 15873146.3.
(Continued)

*Primary Examiner* — Christine H Matthews
(74) *Attorney, Agent, or Firm* — Sughrue Mion, PLLC

(57) ABSTRACT

A magnetic stimulation device includes an excitation coil, a coil driving power supply configured to supply a current having a specific current waveform pattern to the excitation coil, and a coil type detection device configured to distinguish a type of the excitation coil connected to the coil driving power supply, among a plurality of excitations coils. The coil driving power supply includes a control unit configured to control the coil driving power supply to select the specific current waveform pattern among a plurality of current waveform patterns predetermined for each of the plurality of excitation coils, based on the type of the excitation coil distinguished by the coil type detection device and supply the current with the specific current waveform pattern to the excitation coil.

11 Claims, 5 Drawing Sheets

(56) References Cited

U.S. PATENT DOCUMENTS

| | | | |
|---|---|---|---|
| 2008/0262287 A1* | 10/2008 | Dussau | A61N 2/02 600/13 |
| 2008/0275289 A1 | 11/2008 | Olree et al. | |
| 2009/0227831 A1* | 9/2009 | Burnett | A61N 2/02 600/13 |
| 2011/0021863 A1 | 1/2011 | Burnett et al. | |
| 2013/0338424 A1 | 12/2013 | Pascual-Leone et al. | |
| 2014/0235928 A1 | 8/2014 | Zangen et al. | |

FOREIGN PATENT DOCUMENTS

| | | |
|---|---|---|
| JP | 2008-272497 A | 11/2008 |
| WO | 2007/123417 A1 | 11/2007 |

OTHER PUBLICATIONS

Koichi Hosomi et al., "The mechanism of repetitive transcranial magnetic stimulation for central post-stroke pain" Pain Reseach, 2010, pp. 1-8, vol. 25.

J.P.O'Reardon et al., "Efficacy and Safety of Transcranial Magnetic Stimulation in the Acute Treatment of Major Depression: A Multisite Randomized Controlled Trial", Biol Psychiatry, 2007, pp. 1208-1216, vol. 62.

Jens Volkmann, MD, et al., "Introduction to the Programming of Deep Brain Stimulators", Movement Disorders, 2002, pp. S181-S187, vol. 17, Suppl. 3.

International Search Report for PCT/JP2015/085966, dated Mar. 8, 2016.

Yilmaz, B., et al., *The effect of repetitive transcranial magnetic stimulation on refractory neuropathic pain in spinal cord injury*, The Journal of Spinal Cord Medicine, The Academy of Spinal Cord Injury Professionals, Inc., 2014, vol. 37, No. 4, pp. 397-400, (4 pages total).

Delvendahl, I., et al., *The Role of Pulse Shape in Motor Cortex Transcranial Magnetic Stimulation Using Full-Sine Stimuli*, PLOS ONE, Dec. 16, 2014, pp. 1-22, (22 pages total).

* cited by examiner

[Fig. 1]
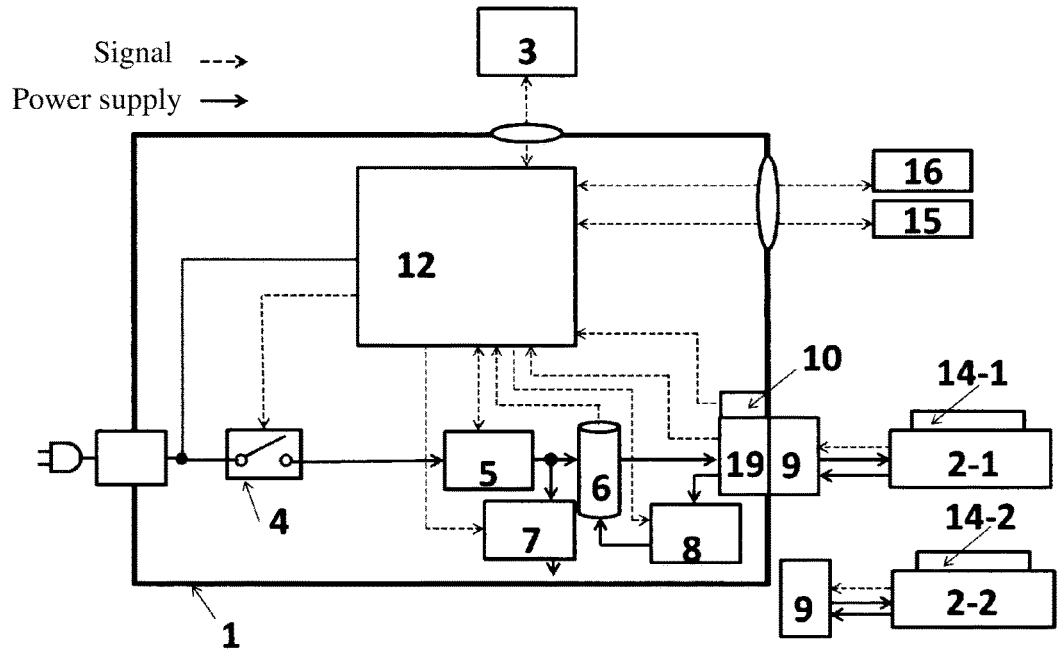
[Fig. 2]
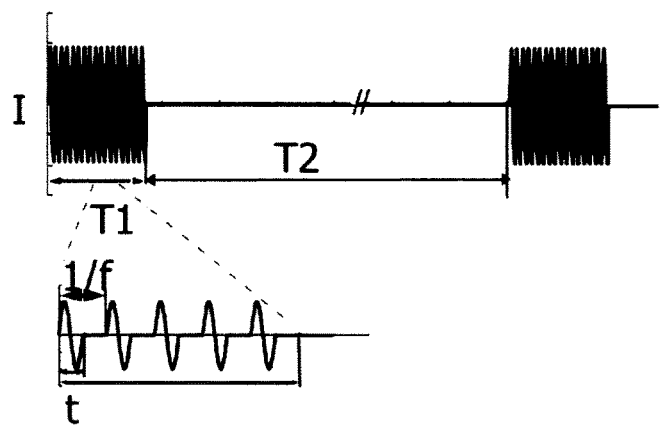
[Fig. 3]
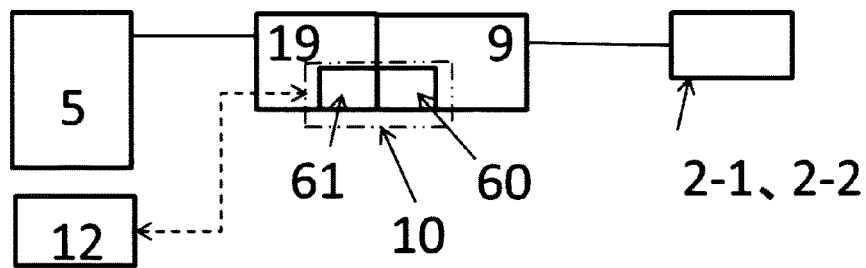

[Fig. 4]
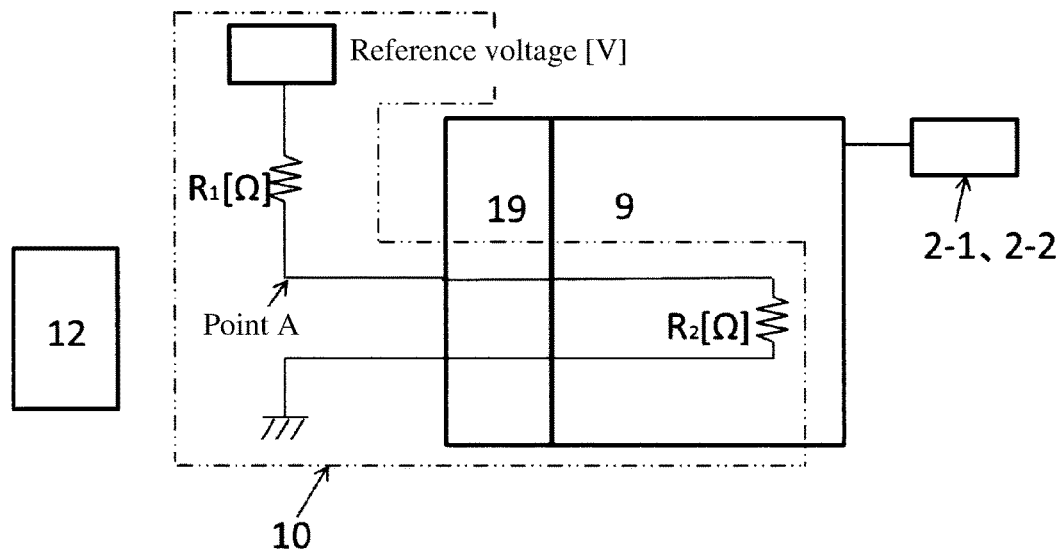
[Fig. 5]
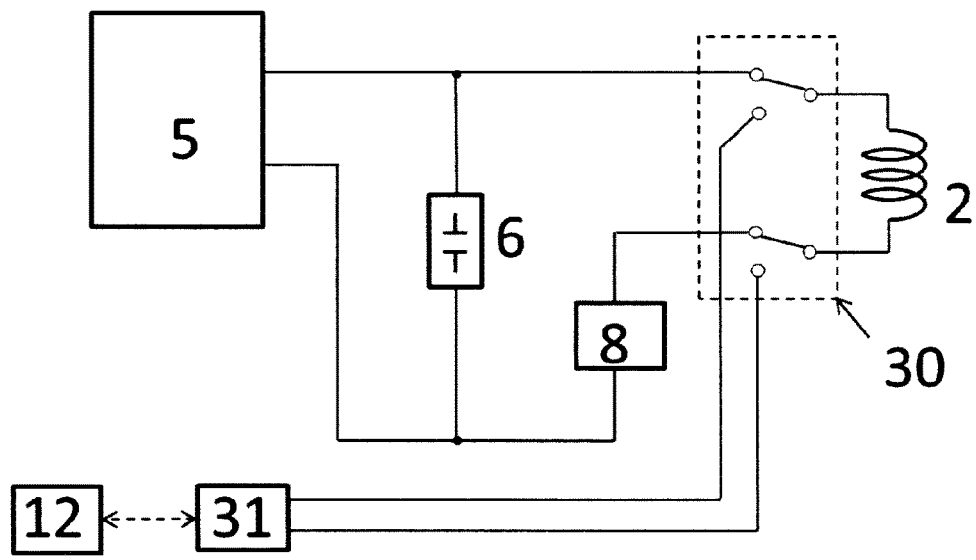

[Fig. 6]
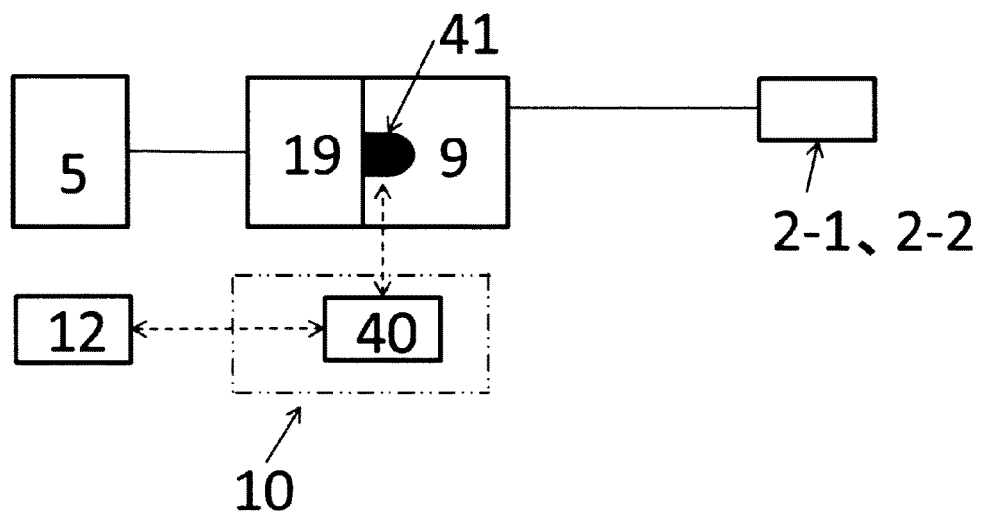
[Fig. 7]
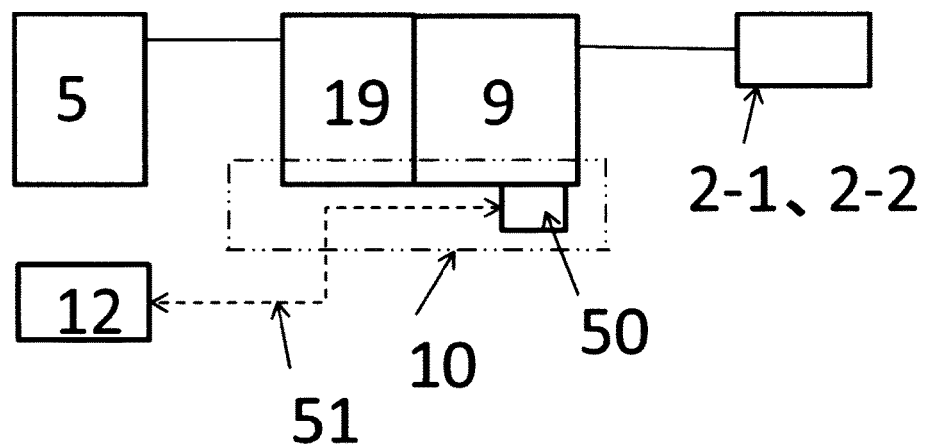

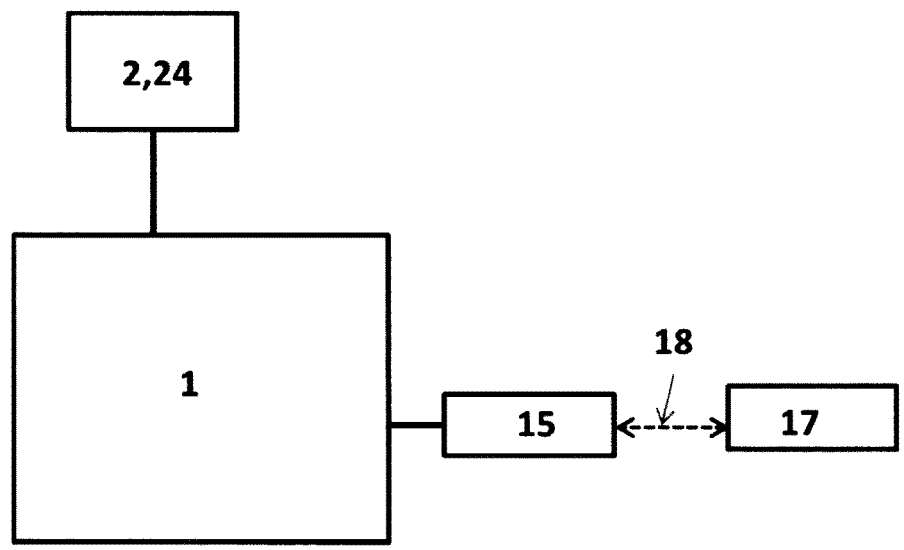
[Fig. 8] (a)
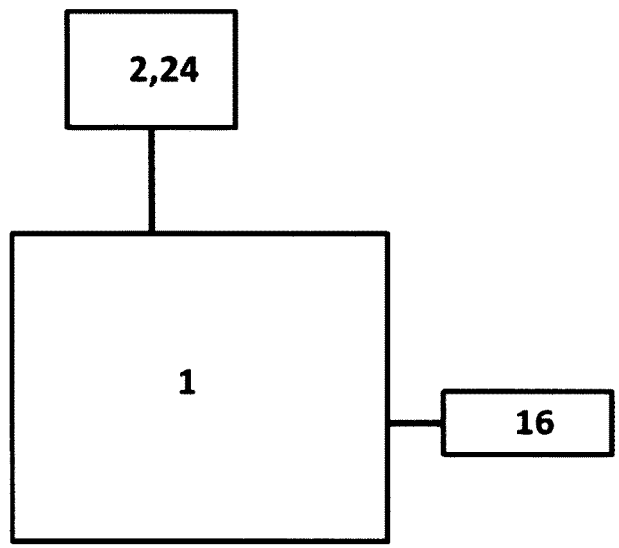
[Fig. 8] (b)

[Fig. 9]
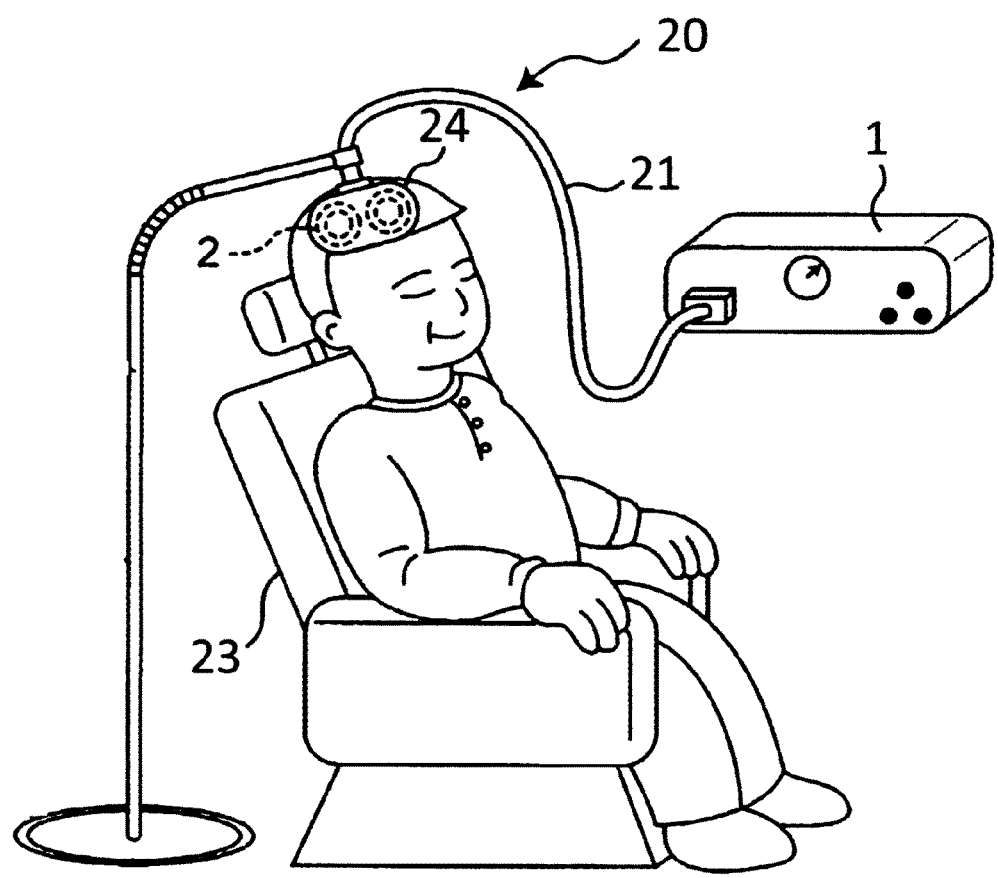

MAGNETIC STIMULATION DEVICE

CROSS REFERENCE TO RELATED APPLICATIONS

This is a National Stage of International Application No. PCT/JP2015/085966 filed Dec. 24, 2015, claiming priority based on Japanese Patent Application No. 2014-262628 filed Dec. 25, 2014, the contents of all of which are incorporated herein by reference in their entirety.

TECHNICAL FIELD

The present invention relates to a magnetic stimulation system, and specifically to a magnetic stimulation device capable of connecting to a plurality of types of excitation coils and applying a specific current waveform pattern to the coil by distinguishing the connected coil type.

BACKGROUND ART

The repetitive transcranial magnetic stimulation (rTMS) which is a kind of magnetic stimulation therapies is a method of treatment that enables to treat, relieve and improve symptoms of neurological disorder such as post-stroke pain, depression and Alzheimer's disease by noninvasively applying magnetic stimulation to a specific region of the brain such as an intracerebral nerve.

In the transcranial magnetic stimulation therapy, a magnetism generation means such as an excitation coil is disposed in a specific position on a surface of a scalp of a patient, and magnetic stimulation is applied to a specific part of the brain of the patient by the magnetism generating means. As a specific method, PTL 1 discloses that stimulation is applied to intracerebral nerve directly under a coil unit disposed on the surface of the scalp of the patient by flowing current through the coil unit to locally produce a minute pulse magnetic field, thereby generating an eddy current in the cranium by using the principle of electromagnetic induction. Magnetic stimulation methods other than a transcranial magnetic stimulation method include, for example, a magnetic stimulation method that performs nerve stimulation to a pelvic floor area.

A magnetic therapy system is usually configured to perform a clinically approved magnetic stimulation therapy, and an excitation pattern therefore is fixed. For example, according to NPL 1, it is described that a treatment condition for post-stroke pain is set at a frequency of f=5 Hz, 10 seconds for a stimulation time, 50 seconds for an interval time, 10 trains, and 90% RMT, and according to NPL 2, a treatment condition for depression is set at frequency f=10 Hz, 4 seconds for a stimulation time, 26 seconds for an interval time, 75 trains, and 120% RMT. In this case the minimum stimulus intensity capable of inducing Motor Evoked Potential (MEP) amplitude with a probability of 50% or more is defined as Motor Threshold (MT), and Resting Motor Threshold (RMT) denotes the MT at rest. These differ in each patient according to magnetic stimulation receptiveness of a patient and are precisely determined by electromyography. These may also be simply determined by observing a condition of muscle contraction (twitch) of the patient at the time of a treatment. Moreover, the treatment condition includes a pulse width t. According to NPL 3, in Deep Brain Stimulation (DBS) it is described that different pulse widths t are utilized depending on treated diseases such as tremor and ataxia, and in rTMS it is similarly assumed that pulse widths t as an optimum treatment condition may differ depending on diseases.

Above described treatment conditions that give a stimulus to cranial nerve are realized by both a coil and a coil driving power supply, and a dedicated coil and an dedicated coil driving power supply are basically required for giving a treatment condition optimum for each disease and each patient. However, preparing the dedicated coil and the coil driving power supply for different diseases results in preparing different magnetic stimulation systems for each of the disease, so that increase in the apparatus purchase cost in a medical institution and a price rise of treatment apparatuses due to high-variety low-volume manufacturing will be incurred.

Devices currently used for clinical study include an inspection apparatus capable of being used with connecting a plurality of coils to one coil driving power supply. In this inspection device, for the above described treatment conditions, after a medical doctor connects a coil corresponding to a disease to the coil driving power supply, the setting apparatus provided in the coil driving power supply is manually adjusted so as to realize a current waveform pattern to be applied to the coil. However, excessive irradiation of a pulse magnetic field has side reaction risks such as an epileptic seizure, and to date, it is thought to be desirable that the inspection device be dealt with by a health-care worker having knowledge to rightly perform operation while understanding magnetic field characteristics generated by the coil through a current provided from the coil driving power supply. In order to make the treatment popular in the future, a function to support setting operations of a health-care worker so that a device can be safely dealt with without advanced knowledge, and moreover a function enabling a patient oneself to operate the device will be required.

CITATION LIST

Patent Literature

[PTL 1]
  WO 2007/123147

Non Patent Literature

[NPL 1]
  Koichi Hosomi, et al. The mechanism of repetitive transcranial magnetic stimulation for central post-stroke pain. PAIN RESEARCH. 25(2010): 1-8
[NPL 2]
  J. P. O'Reardon et al., Efficacy and Safety of Transcranial Magnetic Stimulation in the Acute Treatment of Major Depression: A Multisite Randomized Controlled Trial, Biol Psychiatry, 2007; 62: 1208-1216
[NPL 3]
  Volkmann J. et al., Introduction to the Programming of Deep Brain Stimulation, Movement Disorders, Vol. 17, Suppl. 3, 2002: S181-S187

SUMMARY OF INVENTION

Technical Problem

The purpose of the present invention is to enable a convenient supply of optimal therapeutic conditions on a per disorder and patient basis by making a coil driving power supply identify the type of coil connected thereto and apply a specific current waveform pattern to the coil.

Solution to Problem

The present inventor, in consideration of the above-described problems, has achieved the present invention that can conveniently provide a treatment for different diseases such as neuropathic pain such as post-stroke pain, depression, Alzheimer's disease, and dementia with a plurality of coils and one magnetic stimulation device.

That is, the present invention is a magnetic stimulation device for giving a magnetic stimulation to the body of a patient, comprising at least:
an excitation coil; and
a coil driving power supply for flowing current having a specific pattern through the excitation coil, wherein a magnetic field is generated by applying a specific current waveform pattern to the excitation coil,
wherein the excitation coil can be selected from a plurality of coil types and connected,
wherein a coil type detection means for distinguishing the type of the connected excitation coil is provided, and
wherein a control unit for controlling an operation of the coil driving power supply selects the current waveform pattern predetermined for each of the excitation coil based on the type of the excitation coil distinguished by the coil type detection means and supplies current with the selected current waveform pattern.

In addition, in the present invention, the coil type detection means is provided with one or more coil type identification terminals on the excitation coil side of a connector which connects the excitation coil and the coil driving power supply and a coil type identification terminal detection means other than the excitation coil and the connector of the excitation coil, and preferably distinguishes the type of the current waveform pattern to be generated by detecting the kind of the coil type identification terminal using the coil type identification terminal detection means.

In addition, in the present invention, the coil type identification terminal means is provided with a resistor for identification on the excitation coil side, and preferably distinguishes the type of current waveform pattern to be generated by a divided voltage potential due to resistance of the resistor.

In addition, in the present invention, the coil type detection means is provided with an excitation coil impedance measurement means, and preferably distinguishes the type of current waveform pattern to be generated using a measurement result by the excitation coil impedance measurement means.

In addition, in the present invention, the magnetic stimulation device is provided with a connector shape feature unit having a different shape for each coil current waveform pattern on the excitation coil side of the connector which connects the excitation coil and the coil driving power supply and a connector shape identification means on the coil driving power supply side,
wherein the connector shape identification means identifies the connector shape feature unit, and the coil type detection means preferably distinguishes the type of the current waveform pattern to be generated.

In addition, in the present invention, the coil type detection means is provided with a current waveform pattern code storage means and a current waveform pattern code transmission means on the excitation coil side, the current waveform pattern code transmission means reads the current waveform pattern code stored in the current waveform pattern code storage means, and the coil type detection means preferably distinguishes the type of current waveform pattern to be generated by transmitting a code representing a current waveform pattern of the excitation coil from the current waveform pattern code transmission means to the coil driving power supply through cable, radio, or optical signal.

Further, in the present invention, the current waveform pattern is preferably in a biphasic wave that flows current in a specific direction followed by flowing current in the reverse direction.

Further, in the present invention, a frequency of the current waveform pattern is preferably variable.

Further, in the present invention, a transcranial magnetic stimulation device has a memory function which can store the magnetic field inducing current waveform pattern set to a power supply and an operation result of a device, and these information preferably can be recorded together with biological information separately obtained in the memory function to be used as a treatment log.

Advantageous Effects of Invention

The transcranial magnetic stimulation device of the present invention enables to use different coils for each disease or each patient in one transcranial magnetic stimulation device. The transcranial magnetic stimulation device of the present invention further can automatically select and apply a current waveform pattern to be operated in the excitation coil when connecting one excitation coil to a coil driving power supply, thus enabling facilitation of a setting and prevention of a mistake in the treatment.

FIG. 1 is a schematic block diagram of a magnetic stimulation system of the present invention.

FIG. 2 is a view illustrating an example of a magnetic field inducing current pattern.

FIG. 3 is a schematic diagram of a coil type detection means by a coil type identification terminal.

FIG. 4 is a schematic diagram of a coil type detection means by a resistor.

FIG. 5 is a schematic diagram of a coil type detection means by an impedance measurement means.

FIG. 6 is a schematic diagram of a coil type detection means by a connector shape identification means.

FIG. 7 is a schematic diagram of a coil type detection means by a current pattern code storage and a transmitting means.

FIGS. 8(a) and 8(b) are schematic diagram of an rTMS device having a log function of treatment records.

FIG. 9 is a schematic view illustrating a transcranial magnetic stimulation system.

DESCRIPTION OF EMBODIMENTS

Hereinafter, a transcranial magnetic stimulation system according to embodiments of the present invention will be described with reference to the attached drawings. Although a transcranial magnetic stimulation system suitable for use in medical fields such as post-stroke pain will be described in the following embodiments, the present invention is also applicable to medical fields such as neurosurgery of other pains (particularly intractable neuropathic pain), depression, and Alzheimer's disease and the like, and psychiatry and the like.

In addition, although the terms (for example, "upper surface", "lower surface", etc.) describing a direction or a position are used for the sake of convenience in the following description, those are aimed at facilitating the understanding of the present invention, and the technical scope of the present invention is not limited by the meanings of those terms. Moreover, the following description is only an illustration of one embodiment of the present invention, and the present invention should never be restricted by these embodiments.

In FIG. 9, a transcranial magnetic stimulation system is schematically shown. The transcranial magnetic stimulation system 20 (hereinafter simply referred to as "magnetic stimulation system 20") has the excitation coil 2 (magnetic field generation means) electrically connected to the coil driving power supply 1 through the cable 21. The coil driving power supply 1 connects to an external power supply, etc., and has a booster circuit and a control unit for flowing a current pulse through the excitation coil 2. A patient fixes one's head while, for example, sitting down on the chair 23 for medical treatment, and the excitation coil 2 is disposed at the specific position useful for the medical treatment on the surface of the scalp. The treatments, etc. are performed by applying a magnetic stimulation of a predetermined intensity to the intracerebral nerve of the patient by the coil disposed at the specific position. A control unit of the coil driving power supply 1 controls the current supply to the excitation coil 2, and conventionally known various types can be used. An operator can perform ON/OFF operation of the coil driving power supply 1 and a setting, etc. of a current pulse for determining intensity and a cycle of the magnetic stimulation.

The excitation coil 2 is incorporated into the coil holder, and further accommodated into the coil unit 24. A lower surface (i.e. a surface facing to the scalp surface of the patient) of the coil unit 24 is preferably formed in a concave curved surface shape corresponding to the head shape of the patient. Thus, the coil unit 24 can be smoothly moved along the head surface of the patient. In addition, a top view shape (a shape of the coil unit when the whole coil unit is viewed from the bottom) of a coil unit 24 may be elliptical including a long circle shape and an oval shape, or an egg shape.

In the medical institution, an optimal coil position and posture of the excitation coil 1, in which neuropathic pain of a patient can be reduced most are determined at the time of primary care of the patient by using equipment designated for positioning. The optimal position and the posture of the excitation coil 2 can be easily reproduced from the next medical treatment by a method in which, for example, a marking for positioning is formed on or in the head surface of the patient.

FIG. 1 illustrates a schematic block diagram of a magnetic stimulation system of the present invention. The system has the coil driving power supply 1 for giving a magnetic stimulation in a desired position of a patient's head, the coil 2 (2-1 and 2-2), and the operating unit 3 for setting treatment conditions. The operating unit 3 may be installed in the coil driving power supply or may be an operating unit configured to be separated from the coil driving power supply and provided in the vicinity of an operator. The operating unit 3 has a operating unit interface with which a medical staff or a patient oneself sets treatment conditions, and transmits the set conditions to the control unit 12 of the coil driving power supply 1 in signals. In the coil driving power supply 1, electricity is supplied from commercial power source, and after AC/DC conversion, is boosted at the booster unit 5. The capacitor 6 of the coil driving power supply 1 is charged at the boosted voltage and a constant current, and when the switching module 8 such as a thyristor operates (turns on) by a signal from the control unit 12 of the coil driving power supply 1, the electricity as current flows in the excitation coil 2 from the capacitor 6 through the connector connecting unit 19 and the connector 9, and a magnetic field is generated in the excitation coil, thus performing treatment. The excitation coil 2 is provided with the sensor 14 (14-1 and 14-2), the condition of the sensor 14 is monitored by the control unit 12, and according to the condition, the treatment is stopped when the treatment to a patient is to be stopped. Specifically, the control unit 12 stops the operation of the switching module 8, breaks the relay 4, stops the booster unit 5, and operates the protection circuit 7 for discharging the electric charge of the capacitor 6 to reduce the potential of the capacitor 6. Moreover, the control unit 12 transmits the data of the operational status, etc. of the device to the operating unit 3, the communication line module 15, and the external storage device 16.

There is an optimum magnetic irradiation range and depth for each disease or disease site for the rTMS treatment. Moreover, there is an optimum stimulus intensity for each patient. It is economically desirable to realize a stimulation condition optimum for each disease and each patient with one general power supply for rTMS, and in order to address this, a system is desired that the power supply is capable of adjusting a current pulse to be applied to a coil according to a disease and a condition of a patient.

A schematic diagram of an excitation pattern used for the rTMS treatment is shown in FIG. 2. Due to the resonance phenomenon of the excitation coil 2 and the capacitor 6, the electric charges return to the capacitor 6 again through the switching module 8 (a diode connected parallel to the thyristor.) At this time, a pulse-shaped current flows through the excitation coil. The pulse-shaped current is in a biphasic wave, which in this circuit configuration has a current waveform of one cycle of a sine wave. The frequency of the pulse current is f; the pulse width is t; the time for generating the pulse current at the frequency f is T1; the time for pausing the pulse current is T2; the time T1 for generating the pulse current f and the time T2 for pausing the pulse current together are referred to as a train, and the desired excitation pattern according to a disease is realized by changing the frequency of the pulse current f, the time T1 for generating pulse current, the time T2 for pausing the pulse current, and the number of the train. The treatment stimulus intensity for each patient is realized by adjusting the pulse current I, in other words, the charged voltage at the capacitor 6 is controlled by the control unit 12. Moreover, the frequency f, the time T1 for generating the pulse current, the time T2 for pausing the pulse current, and the number of the train are also controlled by the control unit 12.

With regard to the pulse width t, the relational expression $t=1/f \approx 2\pi\sqrt{L \cdot C}$ is established between a capacitance C of a capacitor and an inductance L of an excitation coil, therefore, when the pulse width is changed to an optimum pulse width t according to a disease, unlike the above described parameter such as the treatment stimulus intensity and the frequency controlled by the control unit 12 of the coil driving power supply, the pulse width is necessary to be set by a combination of the inductance of the excitation coil and the capacity of the capacitor. Here, a pulse width of several tens to several hundred microseconds is realized by replacing the excitation coil to one having a different inductance while the capacitor 6 inside the coil driving power supply being fixed. Besides, replacing the excitation coil is simpler and safer than replacing the capacitor 6 inside the coil driving power supply. The magnetic stimulation device of the present invention judges which coil is connected when the excitation coil suitable for a disease is connected to one coil driving power supply, and the control unit 12 selects the current waveform pattern to be operated in the excitation coil and applies the selected current waveform pattern to the excitation coil, thereby enabling a treatment condition optimum for a disease and a patient. Moreover, the setting of the treatment condition in the operation unit is facilitated or can be omitted by reading out a treatment condition stored by the control unit 12 in advance and operating the device under the condition, thereby preventing operation mistake of a medical worker. Moreover, a treatment condition prescribed by the medical worker can be read out when the coil is connected, so that the treatment is achieved by the patient oneself without an intervention of the medical worker.

In FIG. 3, a schematic diagram of the coil type detection means (coil type detection device) 10 by a coil type identification terminal of the present invention is shown. The connector 9 of a coil is provided with the coil type identification terminal 60, and by the coil type identification terminal detection means (coil type identification terminal detector) 61 provided in the magnetic stimulation systems such as the connector connecting unit 19 or the control unit 12 of the coil driving power supply, other than the excitation coil and the connector 9, the control unit 12 reads out, according to the type of a coil type identification terminal, a coil current waveform pattern and apply the read out coil current pattern to the excitation coil 2. In FIG. 3, the connector connecting unit 19 is provided with the coil type identification terminal detection means 61.

In FIG. 4, a schematic diagram of the coil type detection means 10 according to one embodiment of the present invention is shown, wherein the coil type detection means is a resistor. An example of a circuit configuration is shown, wherein the connector 9 integrated with the excitation coil 2 is connected to the connector connecting unit 19 of the coil driving power supply 1. When the resistance $R_2$ as the coil type identification terminal 60 is provided on the connector side of the coil, the potential to which the reference voltage V is divided by the power supply side resistance $R_1$ and the connector side resistance $R_2$ is detected at the point A. By changing the resistance $R_2$ on the connector 9 side of the excitation coil to a different value for each disease or disease site, the control unit 12 reads out, by using the detected potential, a coil current waveform pattern registered in advance in the control unit 12. The control unit 12 applies the read-out coil current waveform pattern to the excitation coil 2. A short-circuit state and an open-circuit state may be utilized as the resistance $R_2$ on the connector 9 side.

When the divided potential is not detected (judged as an open-circuit state), it is recognized that the excitation coil 2 is not connected, and the protection function of safely stopping the power supply side may be operated. Specifically, the potential of the capacitor 6 is reduced by stopping the booster unit 5 or operating the protection circuit 7 for discharging the electric charge of the capacitor 6.

Moreover, it is also possible that the resistance $R_2$ on the connector 9 side of the coil is changed for each patient. In other words, a resistance specific to a patient is set by using a variable resistor for the resistance $R_2$, and when the coil of the patient is connected, the device operates with the setting of the treatment stimulus pattern and the intensity for the patient. Specifically, the treatment information specific to the patient associated with the divided potential is input in advance to the control unit 12 of the coil driving power supply 1, and the treatment stimulus pattern and the intensity setting specific to the patient are read out based on the potential divided by the connector 9 side variable resistor $R_2$ of the excitation coil. Thus, an intensity setting by a patient oneself becomes unnecessary, and it becomes possible to use the device simply and safely when used especially at home.

In FIG. 5, a schematic diagram of the coil type detection means 10 according to another embodiment of the present invention is shown, wherein the coil type detection means is an impedance measurement means (impedance measurement device). In order to perform a treatment optimum for a disease, a shape of the coil such as the way of winding the coil and the number of turns is changed for each disease. At this time, the control unit 12 detects a difference in the impedance of the coil and utilizes it for reading out, by using the detected value, the coil current waveform pattern registered in advance. The switching circuit 30 for switching the booster unit 5 to the impedance measurement circuit 31 is provided so that the switching circuit 30 is connected to the excitation coil 2, and the impedance of the excitation coil 2 is measured by using the impedance measurement circuit 31. The control unit 12 reads out, by using the detected impedance value, a coil current waveform pattern, optimum for a disease, registered in advance in the control unit 12. In addition, the impedance measurement circuit 31 may measure not only impedance but also a resistance component and an inductance component to utilize it for applying the coil current waveform pattern, read-out by using the value of resistance or inductance, to the excitation coil 2.

In FIG. 6, a schematic diagram of the coil type detection means 10 according to another embodiment of the present invention is shown, wherein the coil type detection means is a connector shape identification means (connector shape identification device). The connector 9 of the excitation coil 2 is provided with the connector shape feature unit 41 having a characteristic shape, and the shape of the feature unit of the connector shape feature unit 41 is detected by the connector shape identification means (connector shape identification apparatus) 40 such as a camera sensor or a photo reflector provided on the main body side, and the control unit 12 reads out, by using the detected result, the coil current waveform pattern registered in advance in the control unit and applies the read-out coil current waveform pattern to the excitation coil 2.

In FIG. 7, a schematic diagram of the coil type detection means 10 according to another embodiment of the present invention is shown, wherein the coil type detection means is a current waveform pattern code storage/transmission means (current waveform pattern code storage/transmission device). The current waveform pattern code storage means 50 such as an IC card is provided on the excitation coil 2 side, and the code signal transmission means 51 transmits a code from the current waveform pattern code storage means 50 to the control unit 12 on the coil driving power supply 1 side through cable, radio, or optical signal, and the control unit 12 having a code signal reception device (not shown) reads out, by using the recognized code, the coil current waveform pattern registered in advance in the control unit and applies the coil current waveform pattern to the excitation coil 2.

FIGS. 8(*a*) and 8(*b*) are schematic diagram of an rTMS device having a treatment record log function according to the present invention is shown. When using the transcranial magnetic stimulation system in a hospital or at home, the treatment records of a patient are recorded and can be utilized for medical prescription. In the treatment records, a date of therapy execution, time, biological information of a patient (for example, data muscle contraction measured by an electromyography or a strain gauge, etc. when the muscle contraction is generated at a hand or a foot by irradiation of a magnetic field), and data in which the patient expressed own physical condition with a judgment index represented by Visual Analog Scale (VAS), etc., as well as treatment conditions recognized by the control unit 12 by using the coil type detection means 10, record of an actual operation of the rTMS device (for example, the number of times of treatment and treatment intensity, whether the device operated normally and completed the treatment normally or not, the duration needed for the treatment and the positioning, and an alarm history (for example, the number of times of errors)) are recorded. Moreover, a configuration of cloud computing is also included, wherein it is made possible that as shown in FIG. 8 (*a*), these treatment records are transferred as data to the record storage place 17 located in a remote place through the communication module 15 and the communication line 18, and a medical staff and a patient simultaneously or mutually check the data, or as shown in FIG. 8 (*b*), these treatment records are output to the external storage device 16 such as an SD card or a USB memory, and the patient brings them at the time of outpatient visit, and the medical staff uses them for checking the data.

REFERENCE SIGNS LIST 1 coil driving power supply
2 excitation coil
3 operating unit
4 relay
5 booster unit
6 capacitor
7 protection circuit
8 switching module
9 connector
10 coil type detection means
12 control unit
14 sensor
15 communication line module
16 external storage device
17 record storage place
18 communication line
19 connector connecting unit
20 transcranial magnetic stimulation system
21 cable
24 coil unit
30 switching circuit
31 impedance measurement circuit
40 connector shape identification means
41 connector shape feature unit
50 current waveform pattern code storage means
51 code signal transmission means
60 coil type identification terminal
61 coil type identification terminal detection means

The invention claimed is:

1. A magnetic stimulation device for providing a magnetic stimulation to a body of a patient, the magnetic stimulation device comprising:
an excitation coil;
a coil driving power supply to which the excitation coil is configured to be connected and which is configured to supply a current having a specific current waveform pattern to the excitation coil, wherein a magnetic field is generated by applying the specific current waveform pattern to the excitation coil, and wherein the excitation coil is configured to be selected from a plurality of excitations coils of different coil types; and
a coil type detection device configured to distinguish a type of the excitation coil connected to the coil driving power supply, among the plurality of excitation coils,
wherein the coil driving power supply comprises a control unit configured to control the coil driving power supply to select the specific current waveform pattern among a plurality of current waveform patterns predetermined for each of the plurality of excitation coils, based on the type of the excitation coil distinguished by the coil type detection device and supply the current with the selected specific current waveform pattern to the excitation coil.

2. The magnetic stimulation device according to claim 1, wherein the coil type detection device comprises:
coil type identification terminal disposed at a connector of the excitation coil; and
a coil type identification terminal detector disposed in the coil driving power supply, and configured to connect to the coil type identification terminal of the connector of the excitation coil and detect information related to the connected coil type identification terminal,
wherein the control unit is further configured to identify the specific current waveform pattern to be supplied to the excitation coil based on the information detected by the coil type identification terminal detector.

3. The magnetic stimulation device according to claim 2, wherein the coil type identification terminal comprises a resistor, and
the control unit is further configured to identify the specific current waveform pattern to be supplied to the excitation coil based on a divided voltage potential due to resistance of the resistor.

4. The magnetic stimulation device according to claim 1, wherein the coil type detection device comprises an excitation coil impedance measurement device, and
the control unit is further configured to identify the specific current waveform pattern to be supplied using a measurement result provided by the excitation coil impedance measurement device.

5. The magnetic stimulation device according to claim 1, wherein the coil type detection device comprises a connector shape identification device,
each of the plurality of excitation coils is provided with a connector comprising a connector shape feature having a different shape for each of the plurality of current waveform patterns, the connector of each of the plurality of excitation coils is configured to connect the plurality of excitation coils to the coil driving power supply,
wherein the connector shape identification device is configured to identify the connector shape feature of the connector of the excitation coil connected to the coil driving power supply, and
the control unit is further configured to identify the specific current waveform pattern to be supplied to the excitation coil based on the identified connector shape feature.

6. The magnetic stimulation device according to claim 1, wherein the coil type detection device comprises a current waveform pattern code storage device disposed at a connector of the excitation coil, the connected configured to connect with the coil driving power supply,
the coil type detection device is further configured to read a current waveform pattern code stored in the current waveform pattern code storage device, and transmit the current waveform pattern code representing the specific current waveform pattern of the excitation coil, to the control unit, through a cable, a radio, or an optical signal, and the control unit is further configured to control the coil driving power supply to supply the current with the specific current waveform pattern based on the current waveform pattern code.

7. The magnetic stimulation device according to claim 1, wherein the specific current waveform pattern is a biphasic wave that flows the current in a specific direction followed by flowing the current in a reverse direction.

8. The magnetic stimulation device according to claim 1, wherein a frequency of the specific current waveform pattern is variable.

9. A transcranial magnetic stimulation system comprising the magnetic stimulation device according to claim 1, the transcranial magnetic stimulation system further comprising:

a memory configured to store, as a treatment log, information related to the magnetic field induced in the patient by the specific current waveform pattern supplied by the coil driving power supply together with biological information of the patient.

10. The magnetic stimulation device according to claim 2, wherein the plurality of excitation coils comprises a plurality of coil type identification terminals, respectively, the plurality of coil type identification terminals being different from each other, and the coil type identification terminal is one of the plurality of coil type identification terminals.

11. The magnetic stimulation device according to claim 1, wherein each of the plurality of excitation coils comprises a plurality of coil type identification terminals, respectively, the plurality of coil type identification terminals being different from each other, each of the plurality of coil type identification terminals is disposed at a connector of each of the plurality of excitation coils, respectively, and provides information related to the type of the excitation coil, each connector configured to connect to the coil driving power supply, and the control unit is further configured to identify the specific current waveform pattern to be supplied to the excitation coil based on the information detected by the coil type detection device from a coil type identification terminal of the connector of the excitation coil connected to the coil driving power supply, among the plurality of coil type identification terminals.

* * * * *